United States Patent [19]

Richter et al.

[11] Patent Number: 5,856,355
[45] Date of Patent: *Jan. 5, 1999

[54] PHARMACEUTICAL COMPOSITION

[75] Inventors: Friedrich Richter, Schönbühl; Michel Steiger, Bern, both of Switzerland

[73] Assignee: Novartis Ag, Basel, Switzerland

[*] Notice: The term of this patent shall not extend beyond the expiration date of Pat. No. 5,681,849.

[21] Appl. No.: 898,348

[22] Filed: Jul. 22, 1997

Related U.S. Application Data

[63] Continuation of Ser. No. 228,841, Apr. 18, 1994, Pat. No. 5,681,849, which is a continuation of Ser. No. 884,681, May 18, 1992, abandoned.

[30] Foreign Application Priority Data

May 20, 1991 [GB] United Kingdom .................. 9110884
May 29, 1991 [GB] United Kingdom .................. 9111477

[51] Int. Cl.$^6$ .................................................. A61K 31/27
[52] U.S. Cl. ........................... 514/481; 514/864; 514/944; 514/947
[58] Field of Search ..................... 514/481, 864, 514/944, 947

[56] References Cited

U.S. PATENT DOCUMENTS

| 4,760,096 | 7/1988 | Sakai et al. ............... 514/944 |
| 5,681,849 | 10/1997 | Richter et al. ............ 514/481 |

FOREIGN PATENT DOCUMENTS

| 11470/92 | 9/1992 | Australia . |
| 0156507 | 10/1985 | European Pat. Off. . |
| 0325949 | 8/1989 | European Pat. Off. . |
| 0385952 | 9/1990 | European Pat. Off. . |
| 0399858 | 11/1990 | European Pat. Off. . |
| 0478456 | 4/1992 | European Pat. Off. . |
| 2265357 | 10/1975 | France . |
| 927706 | 9/1992 | South Africa . |
| 2098865 | 12/1982 | United Kingdom . |
| 2148711 | 6/1985 | United Kingdom . |

OTHER PUBLICATIONS

G. Petranyi, et al., *Antimicrobial Agents and Chemotherapy*, vol. 31, No. 10 pp. 1558–1561 (1987).

T. C. Jones, J. Dermatological Treatment, vol. 1, Suppl. 2, pp. 29–32 (1990).

Lochhead et al., Soap/Cosmetics/Chem. Spec., pp. 28, 29, 32, 33, 84, & 85, May 1987.

*Primary Examiner*—Kevin E. Weddington
*Attorney, Agent, or Firm*—Gabriel Lopez

[57] ABSTRACT

Non-greasy topical solutions, emulsion gels or lotions comprising as the active agent a compound of formula I

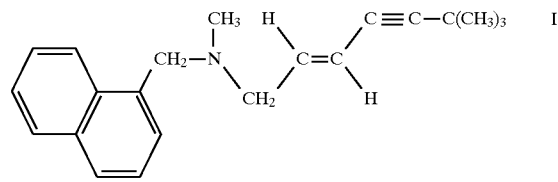

and a lower alkanol, and if desired together with a solubilizing agent or an oil phase such as isopropyl myristate are useful delivery systems.

21 Claims, No Drawings

PHARMACEUTICAL COMPOSITION

This is a Continuation of application Ser. No. 08/228,841, filed Apr. 18, 1994 now U.S. Pat. No. 5,681,849 which is a Continuation of application Ser. No. 07/884,681, filed May 18, 1992, which is now abandoned.

The present invention relates to topical pharmaceutical compositions, such as solutions, gels, fluid gels, emulsion gels and lotions containing an allylamine compound as the pharmacologically active agent.

The present invention provides a topical pharmaceutical composition, comprising as the active agent a compound of formula I

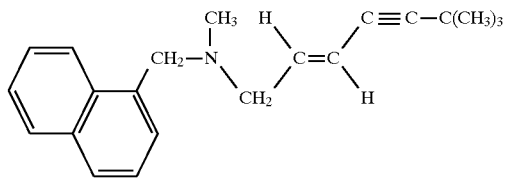

and a lower alkanol.

Such compositions may be for example non-greasy solutions, emulsion gels or lotions, all being liquid or viscous.

In another aspect the present invention provides a process for the preparation of a topical pharmaceutical composition, comprising working up a compound of formula I above together with a lower alkanol and adding further excipients as appropriate.

Examples of topical solutions contemplated under the present invention are solutions per se or are spray liquids, gels or fluid gels.

Water is preferably present in the compositions according to the invention, e.g. in concentrations by weight from e.g. 50 to 85%.

The compound of formula I may be e.g. in free base form or in acid addition salt form. An acid addition salt form may be prepared from the free base form in conventional manner and vice-versa. Examples of suitable acid addition salt forms are the hydrochloride, the lactate and the ascorbate.

The compound of formula I is known from e.g. BE-PS-853976 and EP-A-24587. It belongs to the class of allylamine anti-mycotics. It has the generic name terbinafine and is commercially available under the tradename LAMISIL. Whereas terbinafine is highly active upon both topical and oral application, we have found that the only topical formulation for wide-spread use, a cream in which the drug is kept dissolved in the organic phase, only partly fulfills the patients' needs, as it is only a convenient formulation for selected disease states and skin types. A topical formulation in the form of a composition according to the invention is highly desirable as it offers several advantages e.g. in application properties, in comparison to classical formulations such as creams, e.g.

- faster and more complete release of the drug from the vehicle to the skin and therefore higher efficacy;
- absence of greasiness and no residue upon application and therefore increased convenience for application on haired skin;
- improved spreadability on the skin and thus better convenience for application on larger skin parts; and
- cooling effect on the skin and therefore better convenience for application on seborrhoic skin.

The preparation of topical compositions offering the improved properties mentioned above, however, is difficult with the compound of formula I due to the low solubility of the drug in aqueous systems, the tendency of the compound when used in acid addition salt form or as an oil based emulsion gel or lotion, to separate from the medium as the free base, as droplets or even in crystalline form, as we have found the free base is less soluble in water than the corresponding acid addition salts and due to the tendency of the drug to interact with anionic excipients. Using the acid addition salt form is desirable and also the preferred embodiment of this invention, because the solubility of the drug in aqueous systems may be improved. However, separating of the free base from the equilibrium present in compositions according to present invention presents a serious problem with respect to the reproducability of the pharmacological effect, and to the shelf life stability of such product.

The above difficulties are exacerbated when attempting to prepare one-phase formulations such as fluid gels and gels containing the compound of formula I in free base or salt form in the same phase in combination with the classical Carbomer thickeners (polyacrylic acid derivatives) which is a typical excipient for gels. We have observed that there is an interaction of the components, resulting in an insoluble complex or in crystallization of the base. There is thus a need for improved topical forms e.g. fluid gels and gels.

As outlined above, this problem can according to one aspect of this invention be circumvented by formulating an emulsion system where the free base is dissolved in the oily phase. However these systems may not be suitable for certain kinds of skin type and disease state as in many situations a formulation substantially free of fatty materials such as fatty acids, fatty acid esters and fatty alcohols such as e.g. polyethylene stearates or palmitates, cetyl stearates or palmitates, stearyl or cetyl alcohols, is preferred. A clear solution is also highly desirable as an improved topical formulation. There is thus also a need for such improved forms which are based on water and do not contain oils or fats and wherein the free base present at equilibrium remains in solution.

According to another aspect of the invention, it has now been found that the separation of the free base in water-based solutions may be avoided e.g. for the topical solutions by the addition of suitable solubilizing agents in the formulations, which are non-ionic, e.g. there is no anionic surfactant present. These agents should preferably be surfactants which are water-soluble or water-miscible and compatible with the drug substance and any further excipients present in the formulation, and they should be well tolerated on the skin.

Further, a desirable feature of the contemplated solubilizers is a penetration-enhancing effect for the drug substance without causing any irritation on the skin.

Examples of suitable solubilizing agents for the topical solutions are:

a) Reaction products of a natural or hydrogenated castor oil and ethylene oxide. Such products may be obtained in known manner, e.g. by reaction of a natural or hydrogenated castor oil with ethylene oxide, e.g. in a molar ratio of from about 1:35 to about 1:60, with optional removal of the polyethyleneglycol component from the product, e.g. in accordance with the methods disclosed in DOS 1'182'388 and 1'518'819. Especially suitable are the various tensides available under the tradename Cremophor. Particularly suitable are the products:

Cremophor RH 40 having a saponification number of about 50–60, an acid number <1, an iodine number <1, a water content (Fischer) <2%, an $n_D^{60}$ of about 1.453–1.457 and an HLB of about 14–16;

Cremophor RH 60 having a saponification number of about 40–50, an acid number <1, an iodine number <1, a water content (Fischer) 4.5–5.5%, an $n_D^{25}$ of about 1.453–1.457 and an HLB of about 15–17; and Cremophor EL having a molecular weight (by steam osmometry) of about 1630, a saponification number of about 65–70, an acid number of about 2, an iodine number of about 28–32 and an $n_D^{25}$ of about 1.471.

Also suitable for use in this category are the various tensides available under the tradename Nikkol, e.g. Nikkol HCO-60. Nikkol HCO-60 is a reaction product of hydrogenated castor oil and ethylene oxide exhibiting the following characteristics: acid number of 0.3; saponification number of 47.4; hydroxy value of 42.5; pH (5%) of 4.6; color APHA= 40; M.P.=36.0° C.; freezing point=32.4° C.; H$_2$O content (%, KF)=0.03;

b) polyoxyethylene-sorbitan-fatty acid esters or polysorbates, e.g. of the type known and commercially available under the tradenames Tween (Fiedler 2, p. 1300–1304) and Armotan (Fiedler 1, p. 172) including the products Tween 20 [polyoxyethylene(20)sorbitanmonolaurate];
Tween 40 [polyoxyethylene(20)sorbitanmonopalmitate];
Tween 60 [polyoxyethylene(20)sorbitanmonostearate];
Tween 65 [polyoxyethylene(20)sorbitantristearate];
Tween 80 [polyoxyethylene(20)sorbitanmonooleate];
Tween 85 [polyoxyethylene(20)sorbitantrioleate];
Tween 21 [polyoxyethylene(4)sorbitanmonolaurate];
Tween 61 [polyoxyethylene(4)sorbitanmonostearate]; and
Tween 81 [polyoxyethylene(5)sorbitanmonooleate;

c) polyoxyethylene fatty acid esters, for example polyoxyethylene stearic acid esters of the type known and commercially available under the Tradename Myrj (Fiedler 2, p. 834–835) as well as polyoxyethylene fatty acid esters known and commercially available under the tradename Cetiol HE (Fiedler 1, p. 283–284);

d) polyoxyethylene-polyoxypropylene co-polymers e.g. of the type known and commercially available under the tradenames Pluronic and Emkalyx (Fiedler 2, p. 956–958);

e) polyoxyethylene fatty alcohol ethers, for example polyoxyethylene stearyl ether, oleyl ether, or cetyl ether, e.g. of the type known under the tradename Brij (Fiedler 1, p. 222–224), e.g. Brij 78 and 96, and Cetomacrogol 1000 (Fiedler 1, p. 284).

Preferred solubilizing agents are those under a), b), c) and e), particularly Cetomacrogol 1000®, Cremophor RH40® and Tween 20®. Especially preferred is Cetomacrogol 1000®.

The compound of formula I and the solubilizing agent are preferably present in the topical-solution composition in the proportion of from about 1:0.5 to about 1:15, preferably from about 1:1 to about 1:10 on a w/w basis. The compound of formula I preferably makes up from about 0.1% to about 5%, preferably from about 0.5% to about 2% of the total composition on a weight basis.

In their simplest form the topical solutions of this invention only comprise the drug substance, the solubilizer and the lower alkanolic solvent. The alkanolic solvent is preferably mixed with water when used in a composition according to the invention. Lower alkanolic solvents according to the invention are physiologically acceptable $C_1$–$C_4$ alcohols e.g. isopropanol or preferably ethanol. The concentration by weight of the alkanol in the composition may range e.g. from about 5% to about 90%, e.g. from about 5% to about 35%. A typical concentration is from about 25% to about 45% for a fluid composition, e.g. from 25 to 35%, and for a viscous composition, e.g. a gel from about 5 to about 15%, e.g.10%.

The solutions may be filled into conventional glass bottles with a dropping device or into more elaborate devices, e.g. plastic bottles or plastic bottles with spraying device.

Due to easier application a thickened solution, e.g. a fluid-gel or a transparent gel may be desirable. This can be achieved by adding conventional thickeners to the solutions described above. Suitable components include for example:

polymethylacrylate resins, e.g. of the type known and commercially available under the tradename Eudispert (Fiedler 1, p. 485–486);

cellulose derivatives including e.g. ethyl-, propyl-, methyl- and hydroxypropylmethyl-celluloses;

polyvinyl resins, e.g. including polyvinylalcohols and polyvinyl-pyrrolidones, as well as other polymeric materials including gelatin, alginates, pectins, gum traganth, gum arabicum and gum xanthane;

materials such as silica gel, bentonite, and magnesium-aluminium silicate.

These components when present are suitably present in an amount of up to 20%, more preferably up to 10%, based on the total weight of the composition. Most suitably they are present in an amount of from about 0.5% to about 15%, e.g. from about 1.0% to about 3.0% based on the total weight of the composition.

The topical solution preparations of the invention can be obtained by a process comprising dissolving the compound of formula I in free base form or in acid addition salt form together with the solubilizer in an appropriate vehicle and adding further excipients as appropriate. If a thickened solution or a gel is desired the thickener is added in conventional manner to the system. The process of the invention may be effected in conventional manner.

According to a further aspect of the invention stable emulsion gels and lotions are provided. Where an emulsion gel or a lotion based on a carbomer thickener is required in order to administer the compound of formula I to the skin, the problems associated with the interaction of the free base with the anionic polymer are in principle the same as with the above aqueous solutions. It has now been found that these interactions may be avoided and stable emulsion gels and lotions may be obtained when an oily phase, such as isopropyl myristate, is added to the compound of formula I, preferably in free base form, and the carbomer. This results in stable emulsion gels and lotions which have all the beneficial properties of a gel and avoid the interaction of the drug with the carbomer.

In emulsion gels and lotions according to the invention the compound of formula I and an oil phase are present in the emulsion gels and lotions in the proportion of from about 1:5 to about 1:40, preferably from about 1:7 to about 1:20 on a w/w basis. The oil phase is preferably isopropyl myristate. It is preferably present in a concentration by weight of 10%.

The compound of formula I preferably makes up from about 0.1% to about 5%, preferably from about 0.5% to about 3% of the total composition on a weight basis. Preferably the amount of lower alkanol, water and oil phase, if present, is from about 83 to about 96% by weight of the composition. Conventional further excipients are in particular thickeners such as carbomers (polyacrylic acid derivatives) as known and commercially available under the tradename Carbopol (Fiedler 1, p. 206–207), e.g. Carbopol 934 P or Carbopol 1342. Further excipients are, e.g. emulsifiers such as sorbitan monolaurate (Span 20®) and polysorbate 20 (Tween 20®); however, it has been observed that with the compound of formula I the carbomers stabilize the emulsion to the extent that only little or no emulgator at all is necessary to achieve stable emulsion gels and lotions, particularly when the carbomer is Carbopol 1342.

The resulting emulsion gels and lotions possess improved cosmetic properties, such as facilitated spreading on the skin and absence of greasing; in view of the reduced amount or absence of conventional emulsifiers, they also possess improved pharmacological properties, in particular better tolerability when applied to infected and often inflamed skin. A further advantage of the present invention is that the appearance and consistency of the final formulation may be freely regulated by varying the proportion of thickening agent (carbomer) in the formulation.

The emulsion gels and lotions of the invention may be obtained by a process comprising dissolving a compound of formula I in free base form or in acid addition salt form and further excipients as appropriate, e.g. in an appropriate oil phase such as isopropyl myristate.

The oil phase may be emulsified with an appropriate water phase and then incorporated into a pre-prepared gel concentrate containing the carbomer and further excipients as appropriate. This mode of manufacturing avoids the interaction between the compound of formula I and the carbomer during the process. Preferably the carbomer is neutralized before being mixed with the oil phase.

The formulations may contain additional ingredients, e.g.

complexing agents, e.g. ethylendiamine-tetraacetate (disodium salt);

flavours;

colourants.

The compositions according to present invention may also contain conventional additives to adjust the pH-value to an acceptable value for skin treatment. This may be achieved by adding a pharmaceutically acceptable base or acid and adjusting the pH-value or by adding a pharmaceutically acceptable buffer system to the composition. Additionally, the compositions may contain preserving agents and/or antioxidants, e.g. an amount of 0.05 to 1% by weight of the total weight of the composition, e.g. ascorbyl palmitate, sodium pyrosulfite, butyl hydroxy anisole (BHA), butyl hydroxy toluene (BHT), tocopherols, e.g. α-tocopherol (vitamin E), benzyl alcohol, propyl- or methyl p-hydroxybenzoates.

The compositions of the invention are useful for the same indications as known for other topical compositions, e.g. fungal infections and in the same dosages, e.g. as confirmed by standard clinical trials. Typical effective dosages are achieved when the active agent concentration in the treated skin tissue is between 10 and 10'000 ng per square centimeter. Preferred skin tissue concentrations are between 500 and 2000 ng per square centimeter e.g. 1000 ng per square centimeter e.g. as indicated in standard pharmacological tests. However higher and lower dosages may be effective and may be determined by standard tests. For example the effective concentrations in the treated skin may be achieved when applying e.g. the compound of formula I in form of e.g. a 1% composition according to the invention over the infected area, e.g. 5 mg active agent per day to a skin area of about 100 square centimeters.

The following Examples illustrate the invention. All temperatures are in degrees Centigrade (r.t.=room temperature):

EXAMPLE 1

Topical Solution 1% (Spray 1%)

| Ingredient | Amount (g/100 g) |
| --- | --- |
| Compound I in hydrochloride form | 1.0 |
| Polyethoxy-20-cetylstearyl ether (e.g. Cetomacrogol 1000) | 2.0 |
| Propylene glycol | 5.0 |
| Ethanol 94% w/w | 25.0 |
| Water demineralized | 67.0 |

EXAMPLE 2

Gel 1%

| Ingredient | Amount (g/100 g) |
| --- | --- |
| Compound I in hydrochloride form | 1.00 |
| Disodium edetate dihydrate (e.g. Komplexon III) | 0.02 |
| Polysorbate 20 (e.g. Tween 20) | 2.0 |
| Sodium pyrosulfite | 0.02 |
| Propylene glycol | 0.70 |
| Hydroxypropyl cellulose (e.g. Klucel HF) | 1.50 |
| Ethanol 94% w/w | 35.00 |
| Water demineralized | 59.76 |

EXAMPLE 3

Fluid Gel 1%

| Ingredient | Amount (g/100 g) |
| --- | --- |
| Compound I in hydrochloride form | 1.00 |
| Disodium edetate dihydrate (e.g. Komplexon III) | 0.02 |
| Sodium pyrosulfite | 0.02 |
| Polyethoxy-40-hydrogenated castor oil (e.g. Cremophor RH40) | 1.00 |
| Hydroxypropyl cellulose (e.g. Klucel GF) | 2.00 |
| Ethanol 94% w/w | 35.00 |
| Water demineralized | 60.96 |

EXAMPLE 4

Emulsion Gel 1%

| | Ingredient | Amount (g/100 g) |
| --- | --- | --- |
| A) | Compound I in free base form | 1.00 |
| C) | Butyl hydroxy toluene | 0.02 |
| I) | Sodium hydroxide pellets | 0.10 |
| D) | Benzyl alcohol | 1.00 |
| G) | Carbomer 934 (e.g. Carbopol 934 P) | 1.00 |
| E) | Sorbitan monolaurate (e.g. Span 20) | 1.00 |
| F) | Polysorbate 20 (e.g. Tween 20) | 5.00 |
| H) | Ethanol 94% w/w | 10.00 |
| B) | Isopropyl myristate | 10.00 |
| | Water demineralized | 70.88 |

A pharmaceutically acceptable emulsion gel is obtained from the above ingredients, when the preparation process is carried out in the following steps:

I. A, B, C, D, E and F are mixed together with slight warming until all solid particles are dissolved;

II. in an appropriate vessel or processor containing a stirrer and a homogenizer about half of the water is heated to 60°–70°;

III. I is slowly added to II while stirring and homogenizing until a homogenous emulsion with appropriate droplet size is obtained. The concentrated emulsion is then cooled to r.t.;

IV. in a separate vessel a basic carbomer gel is prepared by dispersing carbomer in H and the second half of the water and neutralizing with I;

V. the basic emulsion III is added to the basic gel and the whole is stirred at r.t. until a homogeneous emulsion gel is obtained.

EXAMPLE 5

Emulsion Gel 1%

|  | Ingredient | Amount (g/100 g) |
|---|---|---|
| A) | Compound I in free base form | 1.00 |
| C) | Butyl hydroxy toluene | 0.02 |
| I) | Sodium hydroxide pellets | 0.10 |
| D) | Benzyl alcohol | 0.50 |
| G) | Carbomer 934 (e.g. Carbopol 934 P) | 1.00 |
| E) | Sorbitan monolaurate (e.g. Span 20) | 1.00 |
| F) | Polysorbate 20 (e.g. Tween 20) | 5.00 |
| H) | Ethanol 94% w/w | 10.00 |
| B) | Isopropyl myristate | 10.00 |
|  | Water demineralized | 71.33 |

A pharmaceutically acceptable emulsion gel is obtained from the above ingredients, when the preparation process is carried out in the following steps:

I. A, B, C, D, E and F are mixed together with slight warming until all solid particles are dissolved;

II. in an appropriate vessel or processor containing a stirrer and a homogenizer about half of the water is heated to 60°–70°;

III. I is slowly added to II while stirring and homogenizing until a homogenous emulsion with appropriate droplet size is obtained. The concentrated emulsion is then cooled to r.t.;

IV. in a separate vessel a basic carbomer gel is prepared by dispersing carbomer in H and the second half of the water and neutralizing with I;

V. the basic emulsion III is added to the basic gel and the whole is stirred at r.t. until a homogeneous emulsion gel is obtained.

EXAMPLE 6

Lotion 1%

|  | Ingredient | Amount (g/100 g) |
|---|---|---|
| A) | Compound I in free base form | 1.00 |
| C) | Propyl p-hydroxybenzoate | 0.03 |
| D) | Methyl p-hydroxybenzoate | 0.10 |
| G) | Ammonia solution 25% w/w | 0.36 |
| F) | Carbomer (e.g. Carbopol 1342) | 0.60 |
| B) | Isopropyl myristate | 5.00 |
| H) | Ethanol 94% w/w | 10.00 |
| E) | Water demineralized | 82.91 |

A pharmaceutically acceptable lotion is obtained from the above ingredients, when the preparation process is carried out in the following steps:

I. A is dissolved in B at r.t.;

II. in an appropriate processor containing a stirrer and an efficient homogenizer C and D are dissolved in E while heating up to 90°. The solution is then cooled to about 30° to 40°;

III. F is dispersed in II. The homogenous dispersion is then neutralized with G, resulting in an opalescent thickened solution;

IV. the organic solution I is then emulsified into the thickened solution III by stirring and homogenizing until a lotion with appropriate droplet size (2 to 20 μm) is obtained;

V. finally H is added to IV and the whole is stirred until the final product is obtained.

We claim:

1. A topical pharmaceutical composition comprising as the active agent a terbinafine compound of formula I

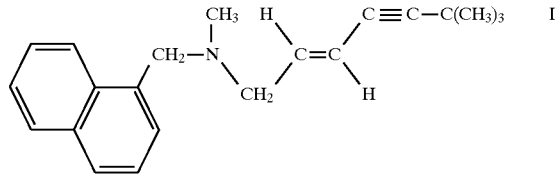

in free base form or in acid addition salt form, water, $C_{1-4}$ alkanol, and a water-soluble or water-miscible nonionic surfactant, wherein no anionic surfactant is present wherein said composition is an emulsion gel or lotion, further comprising an oil phase and a thickener.

2. A composition of claim 1 wherein the thickener is a carbomer.

3. A composition of claim 2 wherein the carbomer is a polyacylic acid derivative.

4. A composition of claim 2 wherein the carbomer is Carbopol 1342.

5. A composition of claim 1 wherein the oil phase is isopropyl myristate.

6. A composition of claim 1 wherein the compound of formula I and the oil phase are present in a proportion of from 1:5 to 1:40 on a w/w basis.

7. A composition of claim 1 wherein the compound of formula I is present in an amount of 0.1% to 5% on a w/w basis.

8. A composition of claim 1 further comprising water.

9. A composition of claim 8 comprising 50 to 85% water, by weight.

10. A composition of claim 8 wherein the amount of alkanol, water, and oil phase is from 83 to 96% by weight of the composition.

11. A composition of claim 1 comprising 5 to 35% alkanol, by weight.

12. A composition of claim 11 wherein the alkanol is ethanol.

13. A composition of claim 1 wherein the compound of formula I is in free base form.

14. A composition of claim 1 substantially free of fatty material.

15. A composition of claim 1 further comprising a non-anionic surfactant.

16. A composition of claim 1 for the treatment of fungal infections wherein the compound of formula I is in free base form or in acid addition salt form, further comprising a solubilizing agent and excipients, as appropriate.

17. A composition of claim 16 wherein the solubilizing agent is a polyoxyethylene fatty alcohol ether.

18. A composition of claim 16 wherein the ratio between the compound of formula I and the solubilizing agent is from about 1:0.5 to about 1:15.

19. A process for the preparation of a composition of claim 1 comprising working up a compound of formula I together with $C_{1-4}$ alkanol and adding further excipients as appropriate.

20. A method for the treatment of fungal infections comprising administering a pharmaceutically effective amount of a composition of claim 1 to a patient in need of such treatment.

21. A topical emulsion gel or lotion pharmaceutical composition comprising a compound of formula I

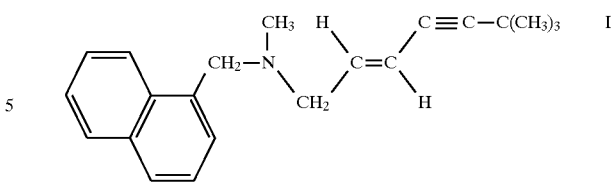

an oil phase, a $C_{1-4}$ alkanol, and a thickener.

* * * * *

UNITED STATES PATENT AND TRADEMARK OFFICE
CERTIFICATE OF CORRECTION

PATENT NO. : 5,856,355

DATED : January 5, 1999

INVENTOR(S) : Richter, et al.

It is certified that error appears in the above-identified patent and that said Letters Patent is hereby corrected as shown below:

Cancel claim 21.

Signed and Sealed this

Ninth Day of March, 1999

Attest:

Q. TODD DICKINSON

Attesting Officer

Acting Commissioner of Patents and Trademarks